US011931194B2

(12) United States Patent
Aoyama (10) Patent No.: US 11,931,194 B2
(45) Date of Patent: Mar. 19, 2024

(54) BODY FLUID ANALYSIS DEVICE, CONTROL METHOD FOR BODY FLUID ANALYSIS DEVICE, AND STORAGE MEDIUM

(71) Applicant: CANON MEDICAL SYSTEMS CORPORATION, Otawara (JP)

(72) Inventor: Gakuto Aoyama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 510 days.

(21) Appl. No.: 17/242,813

(22) Filed: Apr. 28, 2021

(65) Prior Publication Data
US 2021/0369223 A1 Dec. 2, 2021

(30) Foreign Application Priority Data
May 26, 2020 (JP) .................................. 2020-091623

(51) Int. Cl.
*G16H 50/50* (2018.01)
(52) U.S. Cl.
CPC .............. *A61B 6/503* (2013.01); *A61B 6/461* (2013.01); *A61B 6/469* (2013.01); *A61B 6/504* (2013.01)
(58) Field of Classification Search
CPC ......... A61B 6/503; A61B 6/461; A61B 6/469; A61B 6/504; G16H 50/50; G16H 30/40
USPC ....................................................... 382/128
See application file for complete search history.

(56) References Cited

U.S. PATENT DOCUMENTS

| 5,425,365 | A | 6/1995 | Iinuma | |
| 2016/0206260 | A1* | 7/2016 | Wakai | ...................... A61B 8/06 |
| 2016/0220123 | A1 | 8/2016 | Grady et al. | |
| 2016/0220124 | A1 | 8/2016 | Grady et al. | |
| 2020/0065951 | A1* | 2/2020 | Liu | ......................... A61B 8/488 |
| 2021/0228094 | A1 | 7/2021 | Grady et al. | |

FOREIGN PATENT DOCUMENTS

| JP | 3691855 B2 | 9/2005 |
| JP | 2014-503291 A | 2/2014 |
| JP | 6162452 B2 | 7/2017 |
| WO | WO 2012/085797 A1 | 6/2012 |
| WO | WO 2018/159708 A1 | 9/2018 |

OTHER PUBLICATIONS

Japanese Office Action dated Oct. 17, 2023 in Japanese Patent Application No. 2020-091623, 3 pages.
Extended European Search Report dated Oct. 19, 2021 in European Patent Application No. 21175235.7, 10 pages.

* cited by examiner

*Primary Examiner* — Charlotte M Baker
(74) *Attorney, Agent, or Firm* — Oblon, McClelland, Maier & Neustadt, L.L.P.

(57) ABSTRACT

A body fluid analysis device includes processing circuitry. The processing circuitry is configured to set one or more subregions in a region of interest in a medical image. The processing circuitry is configured to set a reference direction for each of the subregions set. The processing circuitry is configured to determine a flow direction of a body fluid for each subregion. The processing circuitry is configured to determine the state of a flow of the body fluid in the region of interest on the basis of the reference direction for each subregion set and the flow direction of the body fluid for each subregion determined.

17 Claims, 10 Drawing Sheets

BODY FLUID ANALYSIS DEVICE, CONTROL METHOD FOR BODY FLUID ANALYSIS DEVICE, AND STORAGE MEDIUM

CROSS-REFERENCE TO RELATED APPLICATION

Priority is claimed on Japanese Patent Application No. 2020-091623, filed May 26, 2020, the content of which is incorporated herein by reference.

FIELD

Embodiments disclosed in the present specification and drawings relate to a body fluid analysis device, a control method for the body fluid analysis device, and a storage medium.

BACKGROUND

In a flow of a body fluid, a flow may be in a normal direction and a flow may be in an abnormal direction depending on a part of a body. For example, in the heart, it is very important to ascertain a direction of blood flow and determine the state of the blood flow since a blood flow in an abnormal direction causes heart failure. In the related art, a method of setting a direction to an apex of a blood vessel as a reference direction and determining the state on the basis of a deviation of a blood flow from the reference direction or a technology of setting a beam direction of ultrasonic waves as a reference direction and determining the state of a blood flow is known.

However, when a region of interest in which a flow of a body fluid is to be determined has a distorted shape or when the region of interest is distorted due to treatment, it may not be possible to accurately analyze the state of a flow of a body fluid in the region of interest.

DETAILED DESCRIPTION

One of problems to be solved by embodiments disclosed in the present specification and drawings is to analyze the state of a flow of a body fluid in a region of interest more accurately. However, the problem to be solved by the embodiments disclosed in the present specification and the drawings is not limited to the above problem. Problems corresponding to respective effects of respective configurations shown in the embodiments to be described below can be positioned as other problems.

A body fluid analysis device includes processing circuitry. The processing circuitry is configured to set one or more subregions in a region of interest in a medical image. The processing circuitry is configured to set a reference direction for each of the subregions set. The processing circuitry is configured to determine a flow direction of a body fluid for each subregion. The processing circuitry is configured to determine the state of a flow of the body fluid in the region of interest on the basis of the reference direction for each subregion set and the flow direction of the body fluid for each subregion determined.

Hereinafter, the body fluid analysis device, the control method for the body fluid analysis device, and the storage medium of the embodiments will be described with reference to the drawings.

Figure 1:
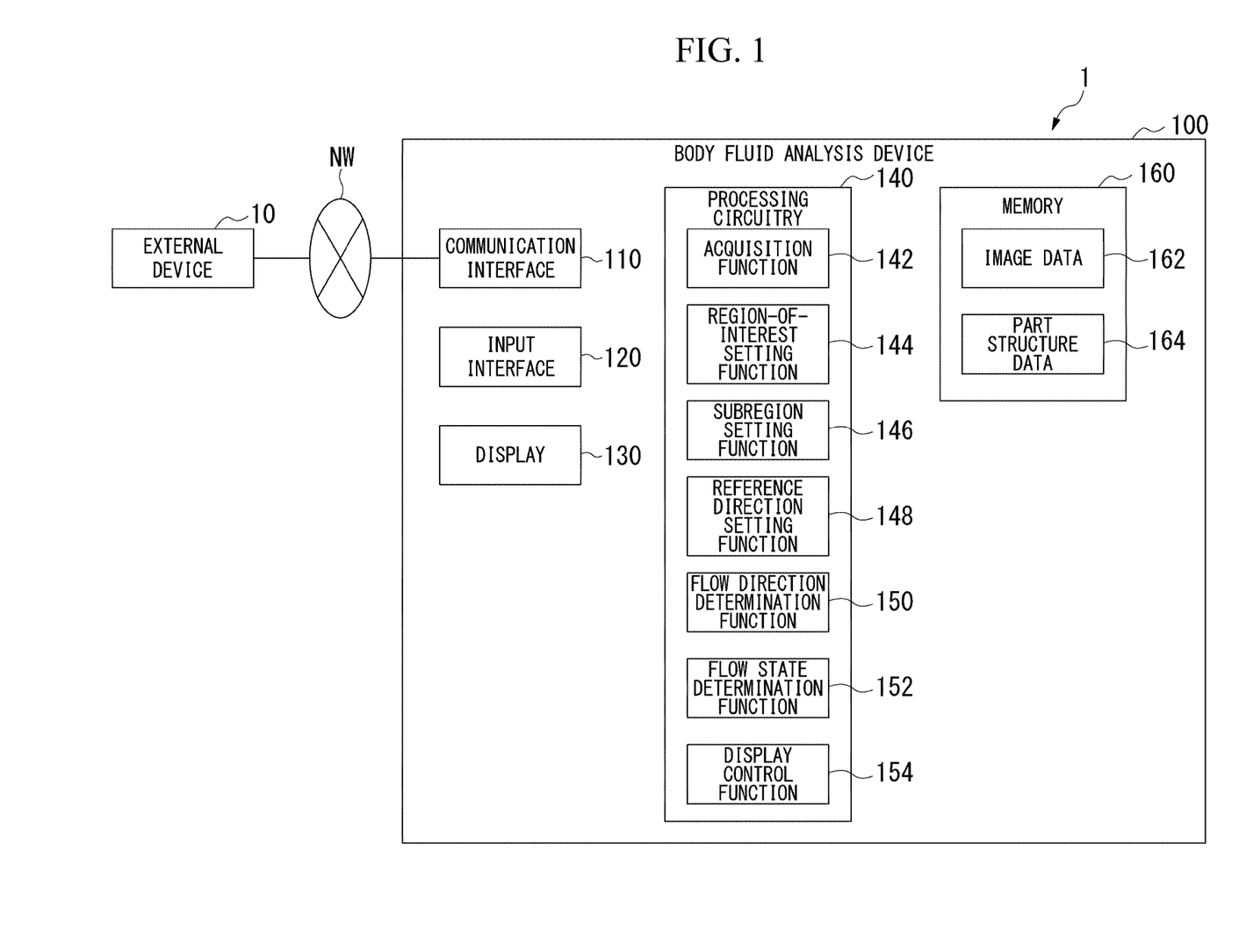
FIG. 1 is a diagram illustrating a configuration example of a body fluid analysis system 1 including a body fluid analysis device of an embodiment.

FIG. 1 is a diagram illustrating a configuration example of a body fluid analysis system 1 including a body fluid analysis device of an embodiment. The body fluid analysis system 1 includes, for example, an external device 10 and a body fluid analysis device 100. The external device 10 and the body fluid analysis device 100 are connected to each other via, for example, a network NW such as a wide area network (WAN), a local area network (LAN), the Internet, a dedicated line, a wireless base station, or a provider. The external device 10 is, for example, an X-ray computed tomography (CT) device, a magnetic resonance imaging (MRI) device, or a nuclear medicine diagnostic device capable of capturing or diagnosing a medical image. Examples of the medical image include an image of a type in which a flow direction of a body fluid in the embodiment can be determined, and an image of a type capable of anatomically aligning with the above image. Examples of the medical image include a CT image, an MRI image, and an ultrasonic image. Further, the external device 10 may be a picture archiving and communication system (PACS), which is a system that manages various types of medical image data, an electronic medical record system that manages an electronic medical record to which a medical image is attached, or the like. Further, the external device 10 may be a storage device such as a storage server or a database.

The body fluid analysis device 100 performs analysis regarding the body fluid using the medical image on the basis of information acquired from the external device 10 via the network NW. Here, a body fluid that is an analysis target in the embodiment is, for example, a fluid substance of which a normal flow direction can be specified at a specific position in a subject (for example, a region of interest in a part such as a blood vessel or an organ). At least one of blood, gastric juice, urine, and cerebrospinal fluid, for example, is included as the body fluid. Further, a solid (including a powder) may be mixed at least in part of the body fluid. Analysis of the body fluid may include, for example, analysis of a state of the body fluid. The state of the body fluid may include, for example, the state of a flow of a body fluid. The state of a flow is, for example, information indicating whether the flow of a body fluid is a forward flow (normal) or a backward flow (abnormal). Further, the state of a flow may include, for example, information on a direction in which the body fluid flows or information on the flow velocity or a flow rate.

The body fluid analysis device 100 includes, for example, a communication interface 110, an input interface 120, a display 130, processing circuitry 140, and a memory 160. The display 130 is an example of a "display". The communication interface 110 includes, for example, a communication interface such as a network interface card (NIC). The communication interface 110 is connected to the external device 10 via the network NW, and performs data communication with the external device 10.

The input interface 120 receives various input operations from a user and outputs the received input operations (operation content) to the processing circuitry 140. For example, the input interface 120 is realized by a mouse, a keyboard, a trackball, a switch, a button, a joystick, a touch panel, or the like. Further, the input interface 120 may be realized by, for example, a user interface that receives a voice input from a microphone or the like. When the input interface 120 is the touch panel, the display 130 to be described below may be formed integrally with the input interface 120. Further, the input interface 120 is not limited to an input interface including a physical operation component such as a mouse or a keyboard, and for example, a processing circuitry that receives a signal corresponding to an input operation from an external input device provided separately from a device and outputs this signal to a control circuitry is also included in examples of the input interface 120.

The display 130 displays various types of information. The display 130 displays, for example, an image generated under the control of the display control function 154, a graphical user interface (GUI) for receiving various input operations from the user, and the like in a predetermined display aspect. For example, the display 130 is a liquid crystal display (LCD), a cathode ray tube (CRT) display, an organic electro luminescence (EL) display, or the like.

The processing circuitry 140 includes, for example, an acquisition function 142, a region-of-interest setting function 144, a subregion setting function 146, a reference direction setting function 148, a flow direction determination function 150, a flow state determination function 152, and a display control function 154. The processing circuitry 140 realizes functions thereof by, for example, a hardware processor executing a program stored in a storage device (the memory 160).

The hardware processor means, for example, circuitry such as a central processing unit (CPU), a graphics processing unit (GPU), application specific integrated circuitry (ASIC), or a programmable logic device (for example, a simple programmable logic device (SPLD), a complex programmable logic device (CPLD), or a field programmable gate array (FPGA)). The program may be directly embedded in circuitry of the hardware processor, instead of being stored in the memory 160. In this case, the hardware processor realizes functions by reading and executing the program embedded in the circuitry. The program may be stored in the memory 160 in advance or may be stored in a non-transient storage medium such as a DVD or a CD-ROM and installed in the memory 160 from the non-transient storage medium by the non-transient storage medium being mounted in a drive device (not illustrated) of the body fluid analysis device 100. The hardware processor is not limited to one configured as a single circuitry, and may be configured as one hardware processor that is a combination of a plurality of independent circuitry to realize each function. Further, a plurality of components may be integrated into one hardware processor to realize each function. The acquisition function 142 is an example of an "acquirer". The region-of-interest setting function 144 is an example of a "region-of-interest setter". The subregion setting function 146 is an example of a "subregion setter". The reference direction setting function 148 is an example of the "reference direction setter". The flow direction determination function 150 is an example of a "flow direction determiner". The flow state determination function 152 is an example of a "determiner". The display control function 154 is an example of a "display controller".

The memory 160 is realized by, for example, a random access memory (RAM), a semiconductor memory element such as a flash memory, a hard disk, or an optical disc. These storage media, including a non-transient storage medium, may be realized by other storage devices connected via the network NW, such as a network attached storage (NAS) or an external storage server device. Further, the memory 160 may include a transient storage medium, such as a read only memory (ROM) or a register. The memory 160 stores, for example, image data 162, part structure data 164, programs, and other information. The memory 160 is an example of a "storage". The image data 162 includes, for example, the medical image acquired from the external device 10. The part structure data 164 is information in which information on an anatomical structure is associated with each of parts such as a blood vessel or an organ in the body. The information on an anatomical structure includes, for example, information obtained by analyzing a shape or a motion of at least a portion of a part on the basis of structure information of the part.

Figure 2:
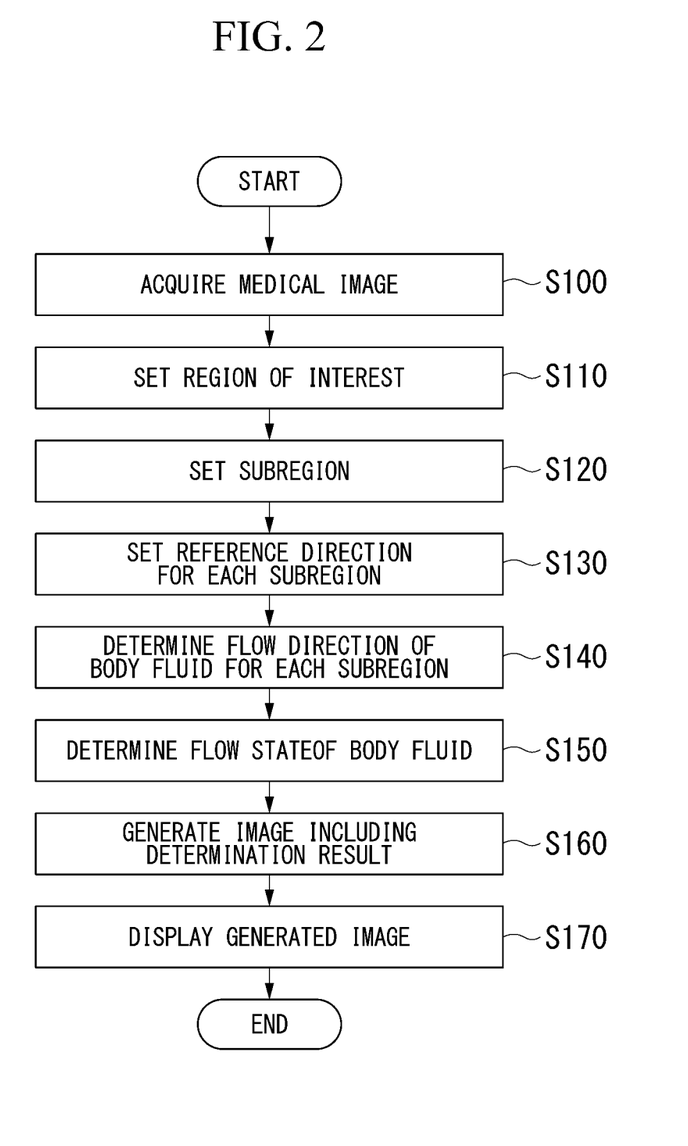
FIG. 2 is a flowchart illustrating an example of a flow of a process that is executed by processing circuitry 140.

Next, a process that is executed by the processing circuitry 140 will be described. FIG. 2 is a flowchart illustrating an example of a flow of a process that is executed by the processing circuitry 140. The process of FIG. 2 may be replaced with an example of a process that is executed by the body fluid analysis device 100 in the embodiment. In the example of FIG. 2, first, the acquisition function 142 acquires the medical image from the external device 10 connected via the network NW (step S100). The acquired medical image may be stored in the memory 160 as the image data 162. The acquisition function 142 may acquire operation content from the user received by the external device 10 or the input interface 120, in addition to acquiring the medical image. Further, the acquisition function 142 may acquire a request from the external device 10 and provide the external device 10 with information such as an analysis result based on the acquired request.

Next, the region-of-interest setting function 144 sets a region of interest of the medical image acquired by the acquisition function 142 (step S110). The region of interest is a region in which analysis of the body fluid of the present embodiment is performed. The subregion setting function 146 then sets one or more subregions with respect to the region of interest (step S120). The reference direction setting function 148 then sets the reference direction in each subregion set by the subregion setting function 146 (step S130).

Then, the flow direction determination function 150 determines the flow direction of the body fluid for each subregion (step S140).

Next, the flow state determination function 152 determines a flow state of blood for each subregion on the basis of the reference direction set by the reference direction setting function 148 and the flow direction of the blood determined by the flow direction determination function 150 (step S150). Then, the display control function 154 generates an image including a determination result of the flow state determination function 152 (step S160), and causes the generated image to be displayed on the display 130 as an analysis result regarding the body fluid (step S170). Hereinafter, the content of each of the processes of steps S110 to S170 will be specifically described.

First, the process of step S110 will be described. For example, the region-of-interest setting function 144 causes the display control function 154 to display the medical image, which is a processing target, acquired by the acquisition function 142 on the display 130. The region-of-interest setting function 144 sets the region of interest for the medical image displayed on the display 130 on the basis of operation content from the user received by the input interface 120 with respect to the medical image displayed on the display 130.

Further, the region-of-interest setting function 144 may set the region of interest for the medical image on the basis of the information on the structure of the part included in the medical image. For example, the region-of-interest setting function 144 performs a process such as binarization or graph cutting on the medical image, and performs image analysis for performing extraction of features, such as luminance extraction and edge extraction based on a processing result. Further, the region-of-interest setting function 144 estimates the portion included in the medical image using feature information obtained through the image analysis and a scheme such as pattern matching using a template of a part prepared in advance. The region-of-interest setting function 144 refers to the part structure data 164 stored in the memory 160 to set the region of interest on the basis of the information on an anatomical structure corresponding to the estimated part. In the following description, a heart is used as an example of the part, and blood is used as an example of the body fluid.

Figure 3:
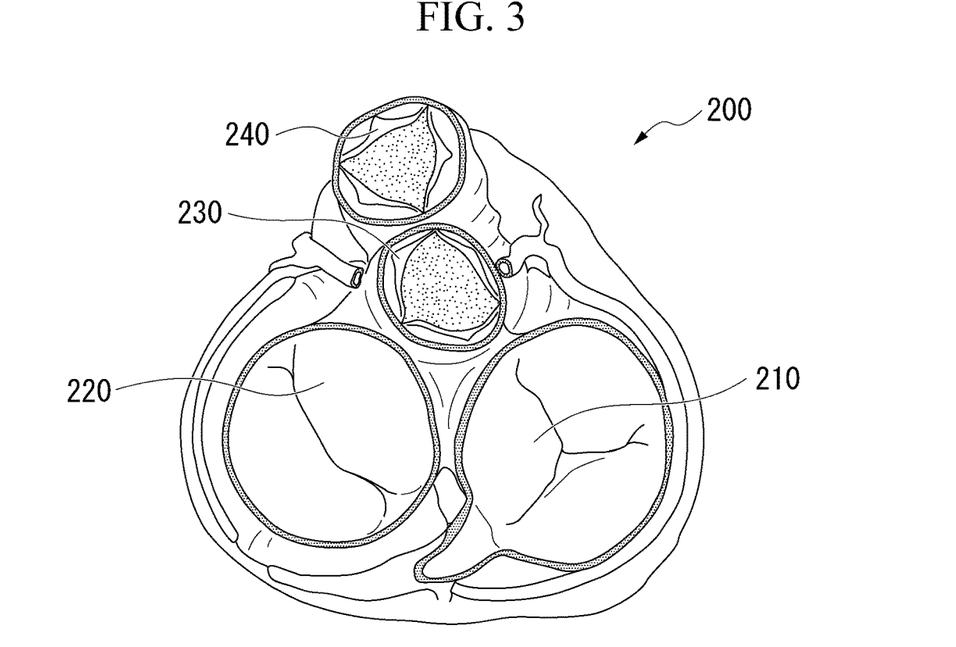
FIG. 3 is a schematic diagram (1) illustrating an anatomical structure of a heart.
Figure 4:
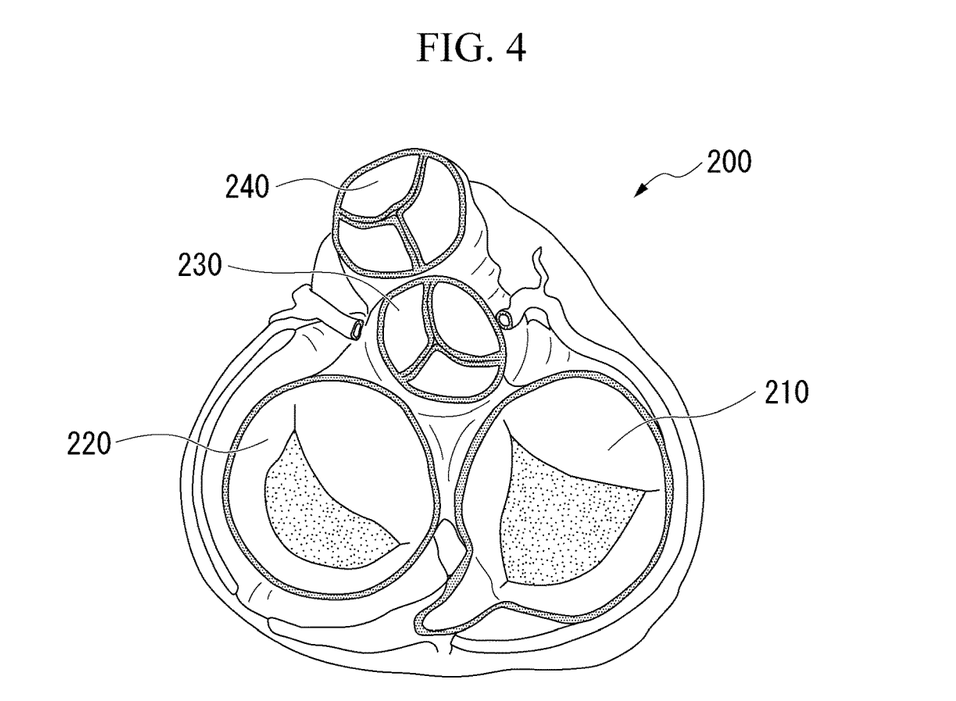
FIG. 4 is a schematic diagram (2) illustrating the anatomical structure of the heart.

FIGS. 3 and 4 are schematic diagrams (1 and 2) illustrating an anatomical structure of the heart. FIGS. 3 and 4 are cross-sectional views illustrating a structure of a heart valve viewed in a direction from a head (an upper part direction) of a human body. FIG. 3 illustrates the state of the valve in a systole of the heart, and FIG. 4 illustrates the state of the valve in a diastole of the heart. As illustrated in FIGS. 3 and 4, there are a tricuspid valve (right atrioventricular valve) 210, a mitral valve (left atrioventricular valve) 220, an aortic valve 230, and a pulmonary valve 240 for preventing a backward flow of the blood in a heart 200. Here, in a normal systole of the heart, the tricuspid valve 210 and the mitral valve 220 are closed and the aortic valve 230 and the pulmonary valve 240 are open, as illustrated in FIG. 3. Further, in a normal diastole of the heart, the tricuspid valve 210 and the mitral valve 220 are released, and the aortic valve 230 and the pulmonary valve 240 are closed, as illustrated in FIG. 4. Thus, since a motion of the heart valve is specified on the basis of the anatomical structure, it is possible to specify a valve orifice region at the time of releasing a valve. The "valve orifice" may also be called a "valve mouth" or a "valve opening".

Figure 5:
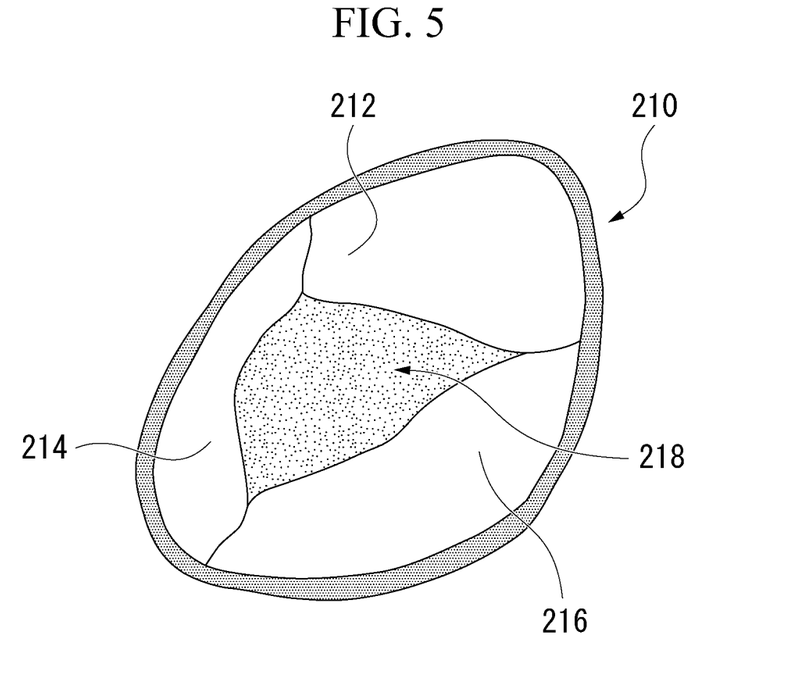
FIG. 5 is a diagram illustrating a region of interest set on the basis of an anatomical structure.

FIG. 5 is a diagram illustrating a region of interest set on the basis of the anatomical structure. In the example of FIG. 5, a schematic view of the structure of the tricuspid valve 210 is shown. The tricuspid valve 210 includes an anterior apex 212, a septal apex 214, and a posterior apex 216. Since blood flows through a valve orifice region 218 formed of the anterior apex 212, the septal apex 214, and the posterior apex 216, the region-of-interest setting function 144 sets the region of interest on the basis of the valve orifice region 218 based on the anatomical structure when the tricuspid valve 210 is included in the medical image. Thus, the region of interest is set on the basis of the anatomical structure of the part included in the medical image, making it possible to set the region of interest for analyzing a flow state of the blood more appropriately.

Further, the region-of-interest setting function 144 may also set the region of interest on the basis of information about a structure of a medical device placed in the body for treatment or diagnosis instead of (or in addition to) the anatomical structure described above. Examples of the medical device include a stent that expands a tubular part of a human body from the inside of a lumen, and an artificial heart valve. Since the medical device can also be identified from the medical image and a shape thereof is specified, it is possible to more appropriately set a nearby region of interest on the basis of the structure of the medical device placed in the body.

The region-of-interest setting function 144 may set a two-dimensional region of interest or may set a three-dimensional region of interest. For example, the region-of-interest setting function 144 sets a cross section (plane) perpendicular to a direction in which the blood vessel extends, as the two-dimensional region of interest. Further, when the region of interest is set on the basis of the valve orifice region, the region-of-interest setting function 144 sets a valve orifice surface at the time of release corresponding to a surface (a valve surface) formed by a valve at the time of closing the blood vessel, which is obtained from the anatomical structure, as the three-dimensional region of interest. This makes it possible to set a region of interest with a distorted shape.

Further, the region-of-interest setting function 144 may set the region of interest from a learning model learned in advance using learning data, instead of (or in addition to) the scheme described above. The learning model is, for example, a model in which machine learning, a neural network, or the like has been used. In the learning model, for example, when feature information obtained from a medical image is input, a region of interest for the medical image is output. The region-of-interest setting function 144 can input feature information of the medical image acquired by the acquisition function 142 to the learning model to acquire the region of interest of the medical image. The learning model may be stored in the memory 160.

Further, the region-of-interest setting function 144 may cause, for example, an image indicating the region of interest set using the anatomical structure or the learning model described above to be displayed on the display 130, and adjust a shape of the region of interest displayed on the basis of operation content received by the input interface 120.

Further, the region-of-interest setting function 144 may set the region of interest on the basis of a size, a shape, and a position on the medical image that have been set for the medical image in advance. Further, the region-of-interest setting function 144 may set an entire region of the medical image as the region of interest. Further, the region-ofinterest setting function 144 may set a plurality of regions of interest for one medical image.

Figure 6:
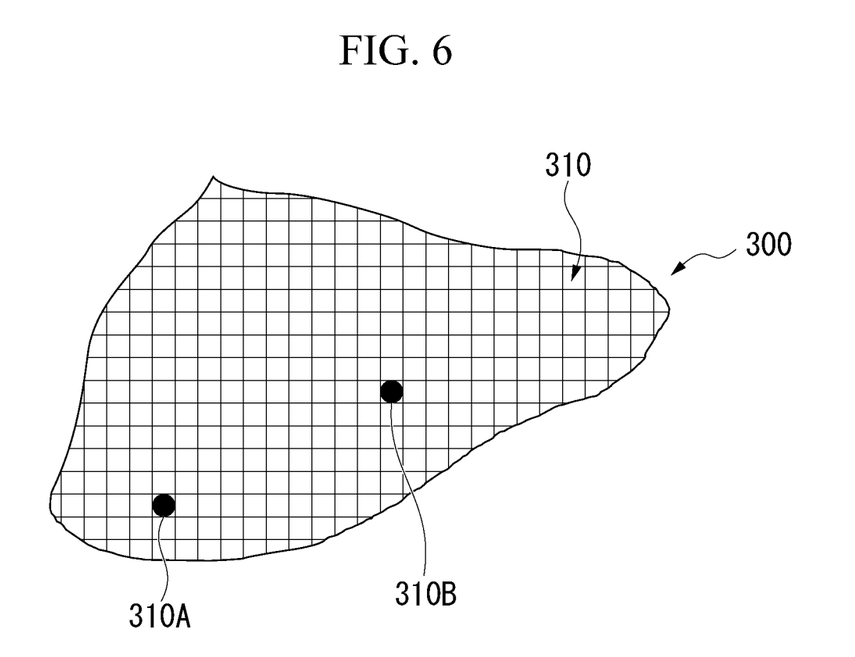
FIG. 6 is a diagram illustrating a subregion setting function 146.

Next, the process of step S120 will be described. FIG. 6 is a diagram illustrating the subregion setting function 146. In an example of FIG. 6, it is assumed that the region of interest 300 is set on the basis of the valve orifice region 218 of the tricuspid valve 210 illustrated in FIG. 5. For example, the subregion setting function 146 sets subregions 310 divided into a grid shape having a predetermined size with respect to the region of interest 300. The size of the grid is set on the basis of, for example, a size of the region of interest 300 or a part of a human body including the region of interest 300.

Further, the size of the grid may be set variably depending on a position of the region of interest 300. For example, it is assumed that change in state of the blood flow is less near a center of the region of interest 300 (for example, within a predetermined distance from the center) than near a region end portion. Therefore, the subregion setting function 146 sets the subregion near the center of the region of interest 300 to be larger than near the region end portion (or sets the subregion near the region end portion to be smaller than near the center). This makes it possible to analyze the state of the blood flow more efficiently and more accurately. Further, the subregion setting function 146 may set a region of one or more grids among a plurality of divided grids as a subregion. Further, the subregion setting function 146 may set the subregion in a shape (a round shape or a rectangular shape) other than the grid.

Figure 7:
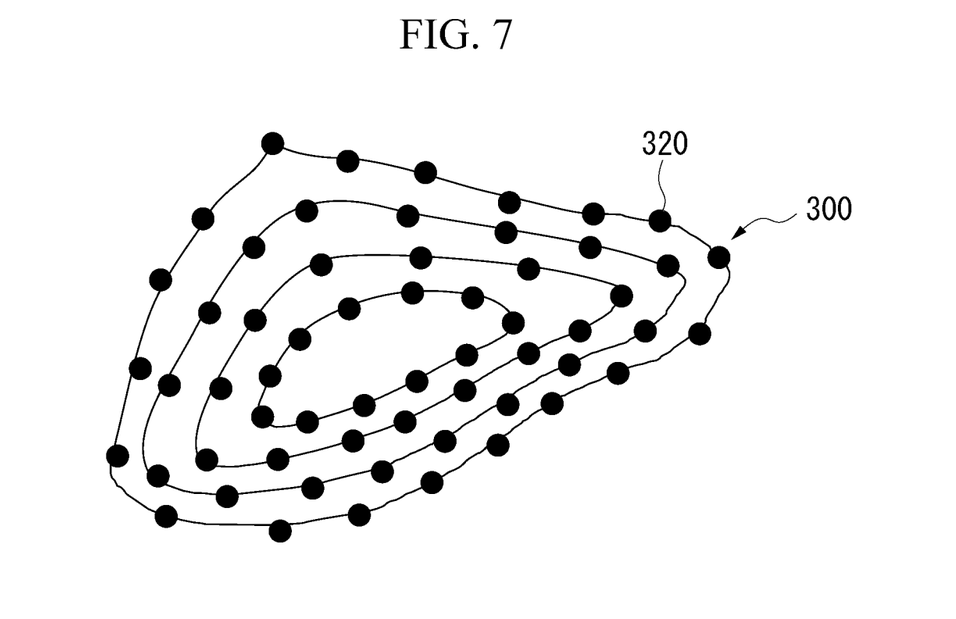
FIG. 7 is a diagram illustrating an example of another setting of a subregion.

FIG. 7 is a diagram illustrating an example of another setting of the subregions. For example, the subregion setting function 146 may concentrically set a subregion 320 on the basis of a contour shape of the region of interest 300, as illustrated in FIG. 7, for example. Further, the subregion setting function 146 may set the subregion 320 on a contour line of the region of interest 300. Further, the subregion setting function 146 may set the subregion 320 concentrically with respect to a center or centroid of the region of interest 300. Further, the subregion setting function 146 may dynamically change and set sizes or the number of the subregions depending on a distance from an end portion (a contour portion) of the region of interest 300.

Further, the subregion setting function 146 may set the subregion in units of pixels of the medical image. Further, the subregion setting function 146 may randomly set a predetermined number of subregions included in the region of interest 300. Further, the subregion may be a predetermined point (for example, a center or a centroid) included in the region.

Further, the subregion setting function 146 may set the subregion on the basis of one or both of the information on the anatomical structure or the structure of the medical device placed in the body, similar to the region-of-interest setting function 144. This makes it possible to set subregions in which analysis of the state of the blood flow is effective for supporting diagnosis of the subject particularly in the region of interest.

Further, the subregion setting function 146 may set the number or positions of the subregions on the basis of operation content of the user received by the input interface 120. In the process according to the embodiment, since a processing cost (for example, processing time, a usage rate of CPU or a memory, or the like) changes greatly depending on the number of subregions, the number or positions of the subregions are caused to be input by the user according to a situation, usage, or the like so that the process can be performed at a more appropriate processing cost.

Figure 8:
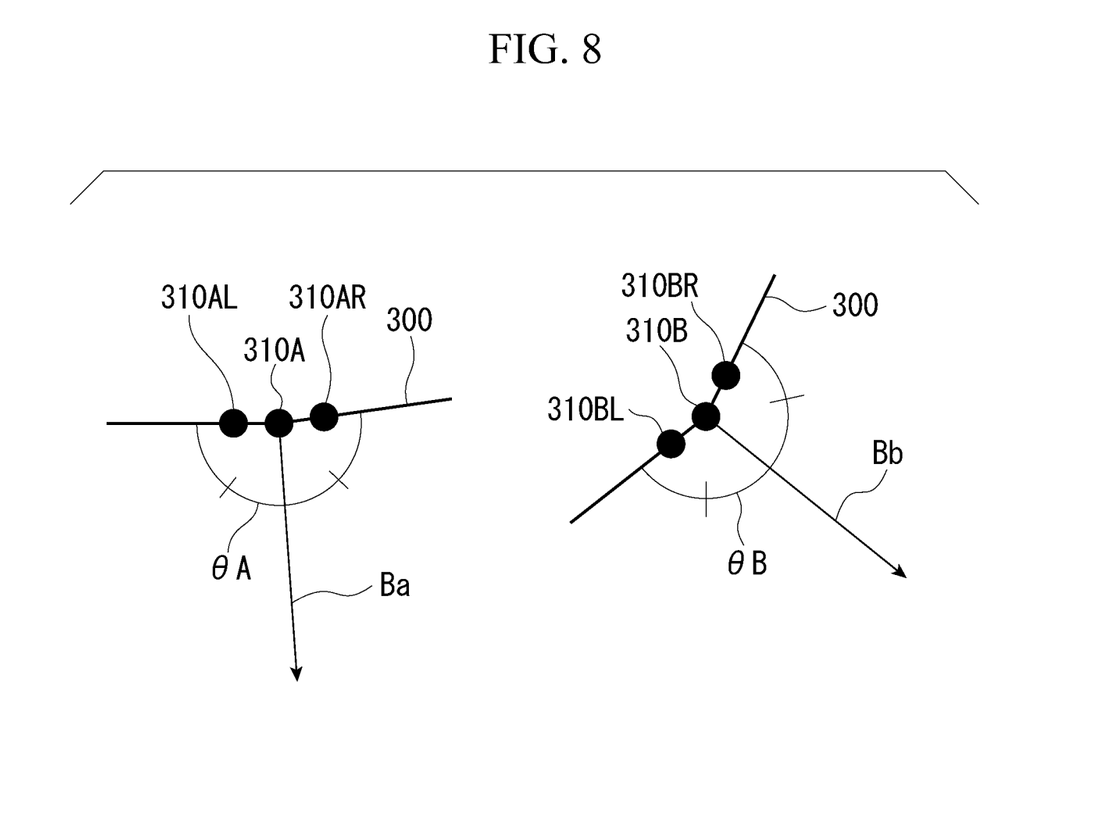
FIG. 8 is a diagram illustrating a reference direction set by a reference direction setting function 148.

Next, the process of step S130 will be described. FIG. 8 is a diagram illustrating the reference direction set by the reference direction setting function 148. In the example of FIG. 8, a relationship between subregions 310A and 310B set in FIG. 6 and the region of interest 300 is illustrated in a simplified manner.

The reference direction setting function 148 sets, for example, the reference direction on the basis of a positional relationship between a subregion that is a target for setting the reference direction (hereinafter referred to as a target subregion) and a subregion around the target subregion. For example, when the region of interest 300 is a two-dimensional (planar) region, a bisector of an angle determined according to a positional relationship of a total of three subregions including the target subregion and subregions located in two directions to the left and right of the target subregion (hereinafter referred to as nearby subregions) is set as the reference direction.

For example, when respective nearby subregions in left and right directions of the target subregion 310A are set as 310AL and 310AR, the reference direction setting function 148 sets a bisector of an angle θA formed by a straight line connecting a center of the target subregion 310A to a center of the nearby subregion 310AL and a straight line connecting the center of the target subregion 310A to a center of the nearby subregion 310AR, as a reference direction Ba. Further, when respective nearby subregions in left and right directions of the target subregion 310B are set as 310BL and 310BR, the reference direction setting function 148 sets a bisector of an angle θB formed by a straight line connecting a center of the target subregion 310B to a center of the nearby subregion 310BL and a straight line connecting the center of the target subregion 310B to a center of the nearby subregion 310BR, as a reference direction Bb. The same process is performed on the respective subregions, making it possible to set an appropriate reference direction for each subregion even when the region of interest is a non-planar (distorted) region.

Further, when the region of interest 300 is a three-dimensional (stereoscopic) region, the reference direction setting function 148 may set six nearby subregions located in multiple directions such as front and back and up and down directions in addition to the two points to the left and right of the target subregion and set the reference direction on the basis of an angle formed by a plurality of straight lines formed according to a positional relationship between the target subregion and the nearby subregions. The nearby subregion may be a subregion adjacent to the target subregion, or a plurality of subregions in one direction viewed from the target subregion may be used. The reference direction setting function 148 may set the reference direction on the basis of operation content of the user received by the input interface 120.

Further, the reference direction setting function 148 may set the reference direction using the anatomical structure instead of (or in addition to) the positional relationship between the target subregion and the nearby subregions. For example, when a valve orifice region of the mitral valve is set as the region of interest, the reference direction setting function 148 extracts regions of a left ventricle and a left atrium through image analysis or the like, and sets the subregion on the basis of a positional relationship between a straight line connecting a center (or centroid) of the extracted region of the left ventricle to a center (or centroid) of the extracted region of the left atrium and each subregion. The reference direction setting function 148 is not limited to the left ventricle or the left atrium, and may set the reference direction on the basis of, for example, a structure of a chordae tendineae, a papillary muscle, or the like. This makes it possible to set the reference direction more appropriately on the basis of a structure (such as a shape) of an entire heart region.

Further, the reference direction setting function 148 may set the reference direction on the basis of a medical image with one time phase or may set the reference direction on the basis of a plurality of medical images having different time phases. For example, since the valve orifice region is deformed due to an operation of the valve when the region of interest is the valve orifice region, a shape of the region of interest is also deformed. Therefore, when the plurality of medical images having different time phases are used, the reference direction setting function 148 associates positions of the respective subregions in the plurality of medical images with each other using an existing deforming and aligning scheme in the plurality of medical images captured at different points in time. The reference direction setting function 148 sets the reference direction in the plurality of medical images in the respective associated subregions. For example, when three-dimensional reference directions at respective points in time T1 to Tm in the subregions are expressed by (T1α, T1β, T1γ) to (Tmα, Tmβ, Tmγ), the reference direction setting function 148 calculates the reference direction of the target subregion using an average value (Σ(Tmα)/m, Σ(Tmβ)/m, Σ(Tmγ)/m) of the reference directions at the respective points in time.

Further, the reference direction setting function 148 may set a distribution of the reference directions for the entire region of interest on the basis of the reference directions for the respective subregions. For example, the reference direction setting function 148 may calculate a normal flow state of the body fluid according to the shape of the region of interest using predetermined numerical fluid analysis or machine learning, and set a distribution in the reference directions on the basis of a result of the calculation. Further, the reference direction setting function 148 may adjust the reference direction in each subregion on the basis of the set distribution of the reference directions. Further, the reference direction setting function 148 may set a reference direction or a distribution of the reference direction of the same part set in the past from execution history data of body fluid analysis executed in the past by the same subject.

Next, a process of step S140 will be described. For example, the flow direction determination function 150 determines a blood direction (the flow direction of the body fluid) using a different scheme depending on the type of medical image. For example, when the medical image is an ultrasonic image, the flow direction determination function 150 determines a blood flow direction on the basis of information obtained by the Doppler effect of the blood flowing through the subregion. Further, the flow direction determination function 150 may acquire information including one or both of the flow velocity or the flow rate of the blood in the subregion on the basis of the information obtained by the Doppler effect. When the medical image is an MRI image, the flow direction determination function 150 determines the blood flow direction in the subregion using a known analysis technique such as 4D-Flow MRI analysis. Further, the flow direction determination function 150 may acquire one or both of the flow velocity or the flow rate of the blood flowing through the subregion from a result of analyzing the MRI image. When the medical image is a CT image, the flow direction determination function 150 determines the blood flow direction from a flow of a contrast medium on the basis of CT images with a plurality of time phases (time series) using the contrast medium. Further, the flow direction determination function 150 may simulate, for example, the blood flow direction from the CT image on the basis of computational fluid dynamics (CFD) analysis.

Further, the flow direction determination function 150 may overall judge the blood flow direction determined using two or more types of medical images among the plurality of types of medical images described above to determine a final blood flow direction. For example, the flow direction determination function 150 may set subregions for the CT image, deform the CT image and the ultrasonic image according to the anatomical structure to align positions of the subregions, and apply the blood flow direction determined using the ultrasound image to the subregions on the CT image. As the deforming and aligning scheme, for example, a known scheme such as a free form deformation (FFD) scheme or a large deformation diffeomorphic metric mapping (LDDMM) scheme can be used.

Figure 9:
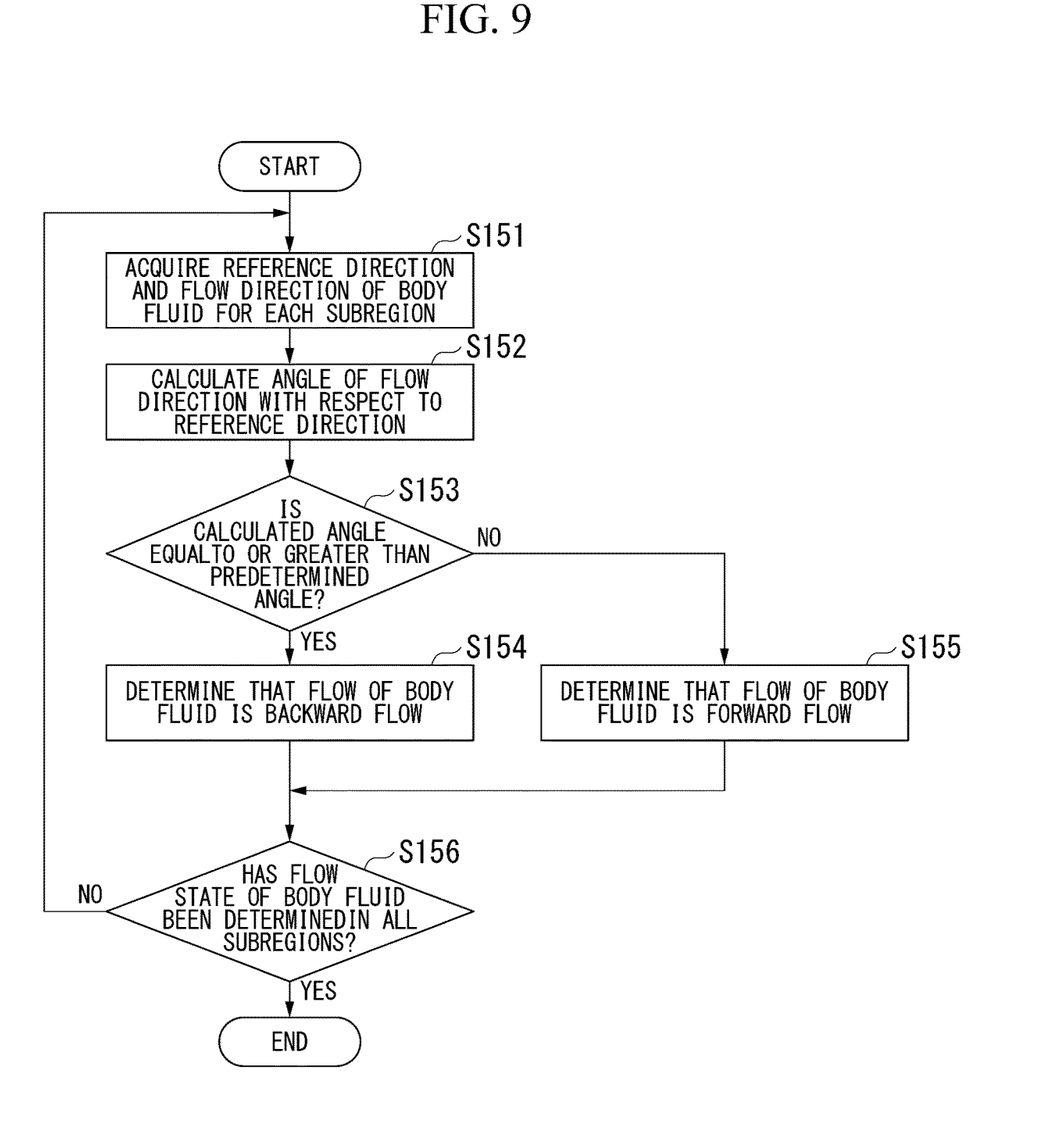
FIG. 9 is a flowchart illustrating a process that is executed by a flow state determination function 152.

Next, the process of step S150 will be described. FIG. 9 is a flowchart illustrating a process that is executed by the flow state determination function 152. The flow state determination function 152 acquires the reference direction and the flow direction of the body fluid (for example, the blood flow direction) for each subregion (step S151), and calculates an angle of the flow direction with respect to the reference direction (step S152). Next, the flow state determination function 152 determines whether or not the calculated angle is equal to or greater than a predetermined angle (step S153). When a determination is made that the angle is equal to or greater than the predetermined angle, the flow state determination function 152 determines that the flow of the body fluid in the target subregion is a backward flow (step S154). Further, when a determination is made that the calculated angle is not equal to or greater than the predetermined angle, a determination is made that the flow of the body fluid in the target subregion is a forward flow (step S155).

After the process of step S154 or step S155, a determination is made whether or not the flow state of the body fluid has been determined for all the subregions (step S156). When a determination is made that the flow state has not been determined in all the subregions, the flow state determination function 152 returns to the process of step S151, sets the subregion in which the flow state has not been determined as the target subregion, and executes the process. Further, when the flow state of the body fluid has been determined in all the subregions in the process of step S156, the process of the present flowchart ends. In the process illustrated in FIG. 9, the determination of the state of the blood flow has been performed for all the subregions, but the present invention is not limited thereto and the determination may be performed on only a predetermined number of subregions or subregions at predetermined positions set in advance.

Figure 10:
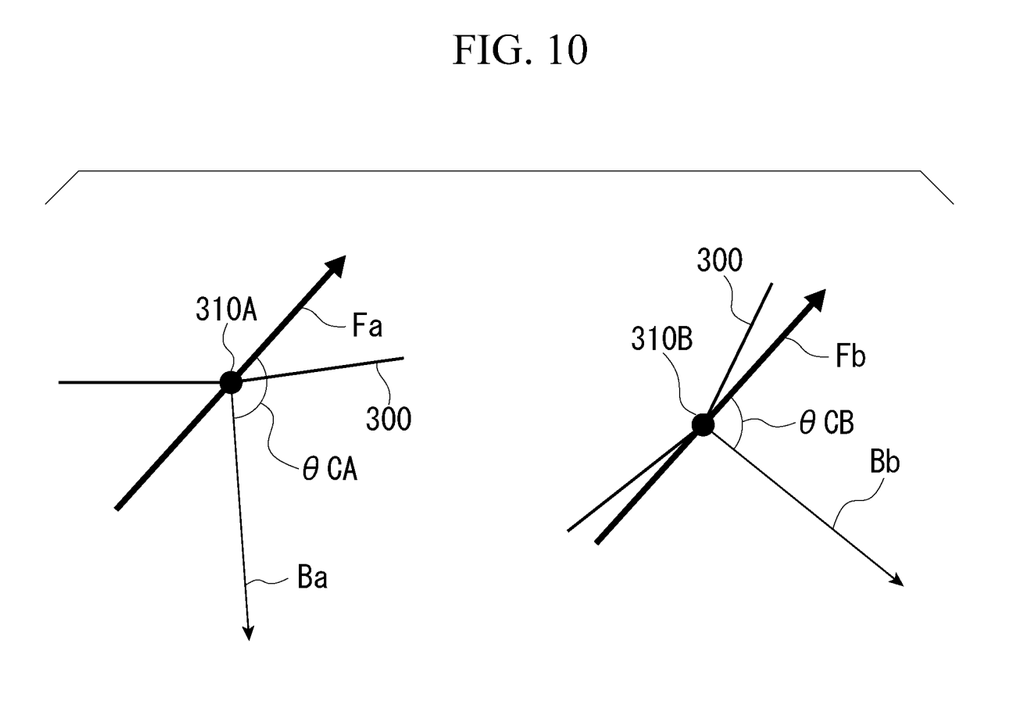
FIG. 10 is a diagram illustrating content of a determination of a flow state of blood for each subregion.

FIG. 10 is a diagram illustrating content of a determination of the flow state of the blood for each subregion. In an example of FIG. 10, a relationship between the subregions 310A and 310B and the region of interest 300 is illustrated in a simplified manner, as in FIG. 8. In FIG. 10, the reference direction Ba and a flow direction Fa of the blood flow with respect to the subregion 310A, and the reference direction Bb and a flow direction Fb of the blood with respect to the subregion 310B are illustrated. The flow state determination function 152 calculates an angle θCA formed by a straight line indicating the reference direction Ba and a straight line indicating the flow direction Fa about the subregion 310A, and determines whether the blood flow passing through the subregion 310A is a forward flow or a backward flow depending on whether or not the calculated angle θCA is equal to or greater than a predetermined angle θTh. The predetermined angle θTh is, for example, an angle at which the blood flow is estimated to pass through a valve orifice surface when the subregion is the valve orifice surface. The predetermined angle θTh may be a fixed angle or may be set variably depending on the region of interest 300 or the subregion. For example, the predetermined angle θTh may be set on the basis of the angle formed by the straight lines connecting the center of the target subregion to the centers of the nearby subregions set in the process of step S130. Further, the predetermined angle θTh may be received by the input interface 120. The predetermined angle θTh generally has a magnitude of 7C (180 degrees) or less.

For example, when the angle θCA is equal to or greater than the predetermined angle θTh as illustrated in FIG. 10, the flow direction Fa of the blood flow becomes a direction in which the blood flow passes beyond the valve orifice surface (the region of interest 300 around the subregion 310A). Therefore, the flow state determination function 152 determines that the flow of blood flow in the subregion 310A is a backward flow.

On the other hand, when an angle θCB formed by a straight line indicating the reference direction Bb and a straight line indicating the flow direction Fa about the subregion 310B is smaller than the predetermined angle θTh, the blood flow does not exceed the valve orifice surface (the region of interest 300 around the subregion 310B) (is downward from a line of the region of interest 300), as illustrated in FIG. 10. Therefore, the flow state determination function 152 determines that the flow of blood flow in the subregion 310B is a forward flow. Thus, the reference direction is set for each subregion and compared with the flow direction of the blood flow, making it possible to determine the state of the blood flow for each subregion with respect to a boundary region with higher accuracy.

Since a swirl flow or a spiral flow is also generated in the blood flow depending on a position of the region of interest through which the blood flow passes, a wrong determination is likely to be performed when the angles θCA and θCB are close to the predetermined angles θTh. Therefore, when the angles θCA and θCB are angles close to the predetermined angles θTh, the flow state determination function 152 may determine that the region is a region in which the state of the blood flow cannot be determined (an undeterminable region).

Figure 11:
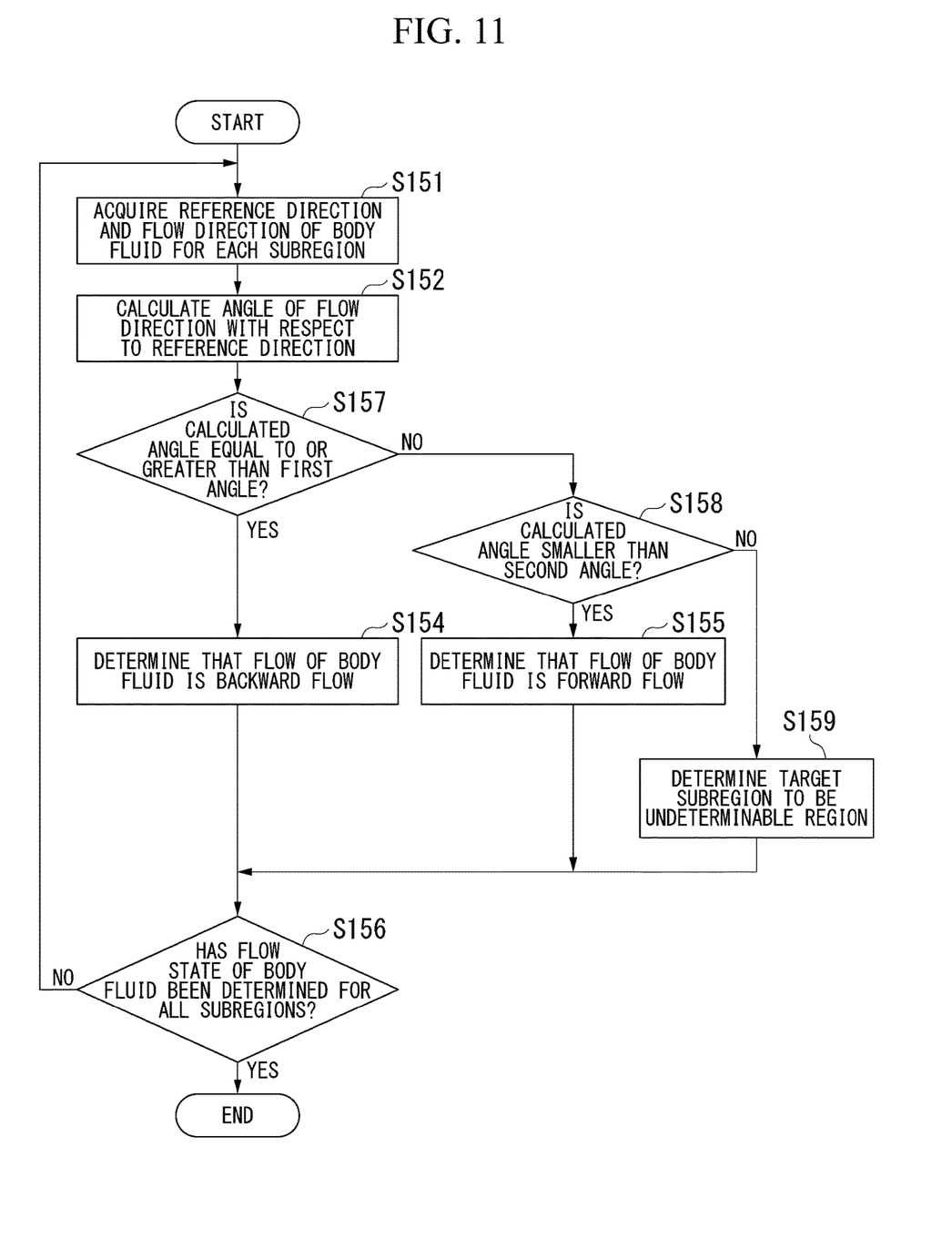
FIG. 11 is a flowchart illustrating a process that is executed by the flow state determination function 152, including a determination of a undeterminable region.

FIG. 11 is a flowchart illustrating a process that is executed by the flow state determination function 152, including a determination of the undeterminable region. The process illustrated in FIG. 11 differs from the processes of steps S151 to S156 illustrated in FIG. 9 in that processes of steps S157 to S159 are added in place of the process of step S153. Therefore, hereinafter, the processes of steps S157 to S159 will be mainly described.

After the process of step S152, the flow state determination function 152 determines whether or not the calculated angle is equal to or greater than the first angle θTh1 (step S157). The first angle θTh1 is an angle that is several degrees to tens of degrees greater than the predetermined angle θTh. When the calculated angle is equal to or greater than the first angle θTh1, the flow state determination function 152 determines that the flow of the body fluid in the target subregion is a backward flow (step S154). When a determination is made that the calculated angle is not equal to or greater than the first angle θTh1, a determination is made whether or not the calculated angle is smaller than the second angle θTh2 (step S158). The second angle θTh2 is a value that is several degrees to tens of degrees smaller than the predetermined angle θTh. When the calculated angle is smaller than the second angle θTh2, the flow state determination function 152 determines that the flow of the body fluid in the target subregion is a forward flow (step S155). Further, since the calculated angle is an angle close to the predetermined angle θTh when a determination is made that the calculated angle is not smaller than a second predetermined angle θTh2, the flow state determination function 152 determines the target subregion to be the undeterminable region (Step S159). According to the process illustrated in FIG. 11, it is possible to clarify a part in which the flow of the blood is ambiguous. Therefore, it is possible to determine the flow state of the blood more accurately on the basis of a result of the subregion other than the undeterminable region.

Further, the flow state determination function 152 may determine the flow state of the blood on the basis of the flow direction of the blood in the target subregion and the nearby subregions instead of determining the flow state of the blood on the basis of the reference direction and the blood flow direction for each subregion. For example, when the flow state of the target subregion is determined to be a backward flow and the flow state of the nearby subregion is determined to be a forward flow, the flow state of the target subregion is changed to a forward flow. For example, there is a place or time in which a special flow such as the swirl flow or the spiral flow occurs locally, in addition to a large flow of the body fluid, in a specific region of the human body. Therefore, the flow state of the blood in the target subregion is changed on the basis of the flow state of the surroundings as described above, making it possible to curb change in result of determining the flow state of the blood when the special flow such as the swirl flow or the spiral flow has occurred. The nearby subregions may be, for example, regions within a predetermined distance from the target subregion, or may be a predetermined number of nearby subregions in order of proximity to the target subregion.

Further, the flow state determination function 152 may determine the flow state of the blood in the target subregion on the basis of a position of the target subregion in the region of interest in addition to the reference direction and the blood flow direction. For example, since it is estimated that the swirl flow, the spiral flow, or the like due to the operation of the valve is less than that at the region end portion when the position of the target subregion in the region of interest is near the center of the region of interest, the flow state determination function 152 curbs change in the flow state of the blood in the target subregion based on the flow state of the blood of the nearby subregion described above. Thus, a determination criterion is changed on the basis of the position of the target subregion in the region of interest, making it possible to determine the flow state of the blood in the subregions or the entire region of interest more appropriately.

Further, the flow state determination function 152 may determine the flow state of the blood on the basis of one or both of the flow velocity or the flow rate of the blood that passes through the target subregion in addition to the reference direction and the blood flow direction. For example, the flow state determination function 152 may determine the state of the flow of the blood with respect to a subregion in which the flow velocity or the flow rate is equal to or higher than a threshold value. This makes it possible to determine the flow state is high for a region in which the flow of the blood and thus, it is possible to more accurately determine whether the blood flow is a forward flow or a backward flow. Further, the flow state determination function 152 may adjust the predetermined angles θTh (the first angle θTh1 and the second angle θTh2) depending on a magnitude of a flow rate and a flow velocity. For example, the flow state determination function 152 widens an angle range from the first angle θTh1 to the second angle θTh2 when the flow rate or the flow velocity increases, and narrows the angle range when the flow rate or the flow velocity decreases.

Further, for example, when the plurality of medical images having different time phases are used as described above, the flow state determination function 152 may set the angle range as a range from a maximum value to a minimum value in the reference direction at points in time T1 to Tm. Further, the flow state determination function 152 may set the angle range in each subregion on the basis of movement information such as a magnitude of an amount of fluctuation in the reference direction at points in time T1 to Tm in each subregion or a magnitude of an amount of movement of the subregion. For example, since it is estimated that an amount of movement of the blood is large in the subregion in which the amount of fluctuation in the reference direction in a predetermined time series is large, the angle range is widened, and since it is estimated that the amount of movement of the blood is small in the subregion in which the amount of fluctuation in the reference direction is small, the angle range is narrowed. This makes it possible to perform the determination of the flow state more appropriately depending on the flow velocity or the flow rate of the blood.

Further, the flow state determination function 152 may perform a determination for supporting diagnosis on the basis of the flow state of the blood in the region of interest. The determination for supporting diagnosis is, for example, a determination of an estimated disease name (for example, heart failure, valve insufficiency, or the like), a probability of illness in the future, or the like.

Figure 12:
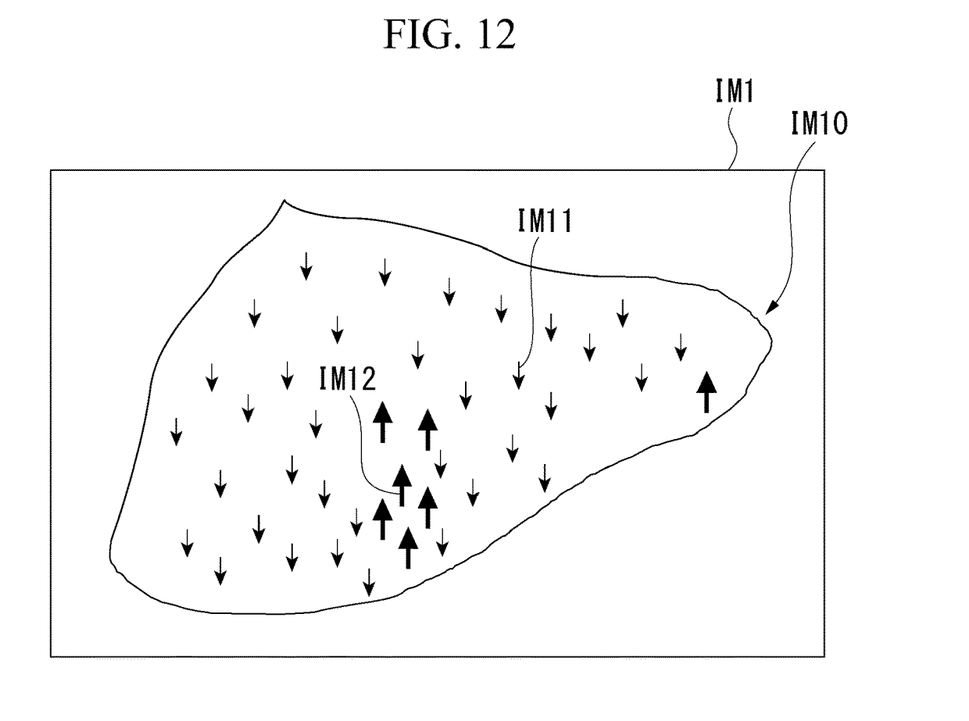
FIG. 12 is a diagram illustrating an example of an image IM1 that is generated by a display control function 154.

Next, the processes of steps S150 and S170 will be described. FIG. 12 is a diagram illustrating an example of an image IM1 that is generated by the display control function 154. In the image IM1, images IM11 and IM12 indicating a flow state positioned in the subregion are displayed so that the images IM11 and IM12 are superimposed on an image IM10 indicating the region of interest 300. The image IM1 may be a medical image including the region of interest 300.

For example, the display control function 154 causes an image indicating the flow state of the blood for each subregion determined by the flow state determination function 152 to be superimposed in association with the position of the subregion in the image IM10 indicating the region of interest. In this case, the display control function 154 superimposes different images so that a difference in the state of the blood flow can be visually recognized. In the example of FIG. 12, the image IM11 indicating that the state of the blood flow is a forward flow and the image IM12 indicating that the state of the blood flow is a backward flow are displayed in different display aspects. The different display aspects are aspects in which it is possible to visually recognize that types of images differ depending on, for example, color or a pattern, gradation, line type, shape, size (thickness), orientation, transmittance, or a degree of emphasis of the images. This makes it possible to ascertain the state within the region of interest 300 with higher accuracy.

Further, the display control function 154 may cause the images IM11 and IM12 indicating the flow states not to be displayed for all the subregions, but may cause the images IM11 and IM12 indicating the flow states, of which some have been thinned out, to be displayed. Further, the display control function 154 may display only an image indicating a predetermined flow state (for example, backward flow) so that the image is superimposed on the image IM10 indicating the region of interest.

Figure 13:
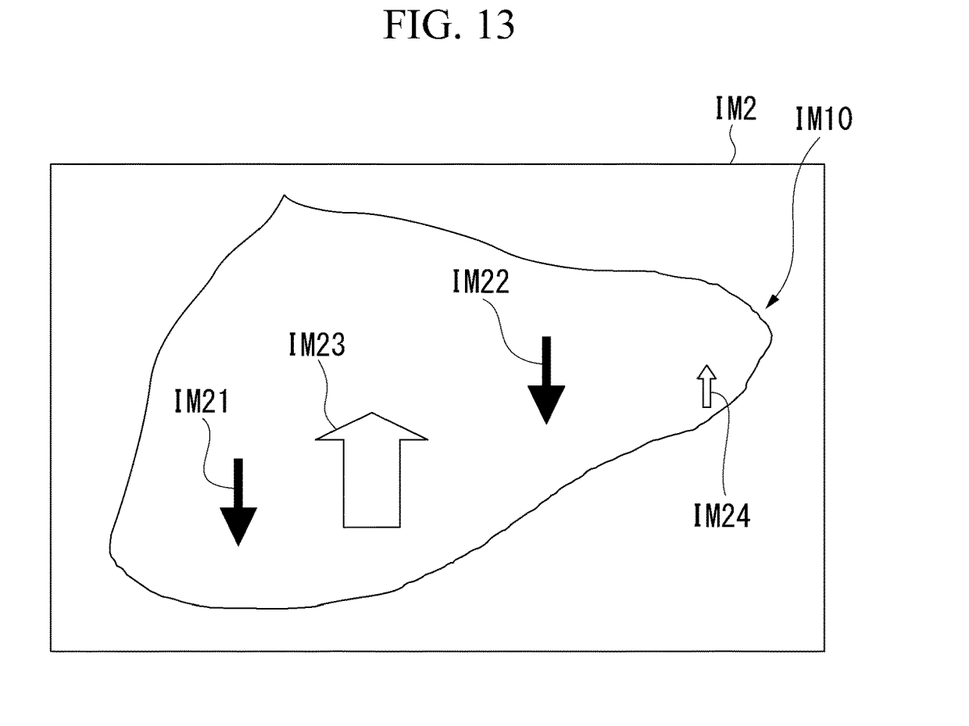
FIG. 13 is a diagram illustrating an example of an image IM2 including a flow state of blood in which some of surroundings have been aggregated.

Further, the display control function 154 may aggregate the flow states in the surroundings (a predetermined region) and generate an image indicating the aggregated flow states. The predetermined region is, for example, a region that includes a plurality of subregions and is present below the region of interest. Further, the predetermined region may be set on the basis of a shape or size of the region of interest, or a fixed region such as a central region of the region of interest may be set. Further, the number of predetermined regions may be a fixed number, or may be set on the basis of an operation content received by the input interface 120. FIG. 13 is a diagram illustrating an example of the image IM2 including an aggregated flow state of the blood. In the example of FIG. 13, when the flow states of the blood illustrated in FIG. 12 are aggregated in the nearby region, images IM21 and IM22 indicating the forward flow and images IM23 and IM24 indicating the backward flow are displayed so that the images are superimposed on the image IM10 indicating the region of interest.

For example, when different flow states are present in the flow states of the blood for the respective subregions included in the predetermined regions, the display control function 154 may overall judge the respective flow states and determine the flow state of the blood for each predetermined region. For example, when a determination is made that the flow state of the target subregion in the predetermined region is a backward flow and the flow state of the nearby subregion is a forward flow, the flow state of the target subregion is updated into a forward flow. The update may be set not to be performed a predetermined number of times or more. The predetermined number of times may be a fixed number of times or may be a variable value received by the input interface 120.

Further, the display control function 154 may compare the number of the subregions determined to be of a backward flow with the number of the subregions determined to be of a forward flow, and set the flow state of the body fluid determined to be a greater number as the flow state of the entire region of interest. Further, the display control function 154 may determine the flow state of the entire region of interest on the basis of a distribution of measurement regions determined to be of a forward flow or of a backward flow. This makes it possible to provide the user with a rough flow state at a position within the region of interest more clearly.

Figure 14:
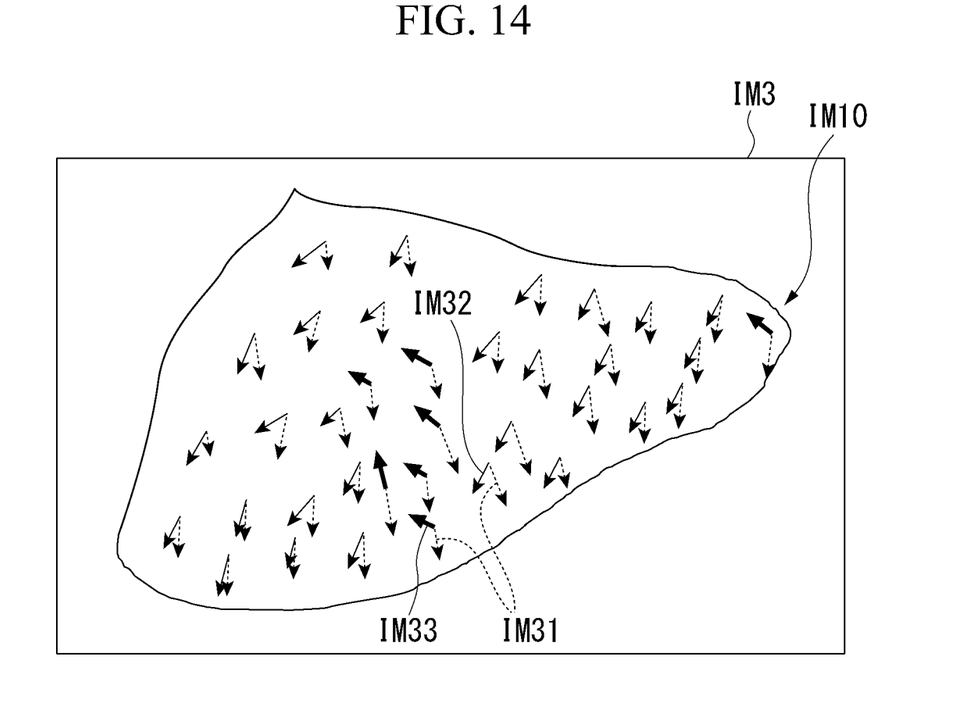
FIG. 14 is a diagram illustrating one of images IM3 including an image indicating a reference direction.

Further, the display control function 154 may cause an image indicating the reference direction of the subregion in addition to the image indicating the flow state of the blood to be displayed. FIG. 14 is a diagram illustrating one of images IM3 including an image indicating the reference direction. In the image IM3, an image IM31 indicating the reference direction with respect to the subregion, an image IM32 indicating that a blood flow is a forward flow, and an image IM33 indicating that the blood flow is a backward flow are displayed so that the images are superimposed on an image IM10 indicating a region of interest. The display control function 154 makes it possible to more clearly confirm a relationship between the reference direction and the blood flow direction by causing the image IM3 to be displayed. Therefore, it is possible for the user to more clearly ascertain properties of the flow state of the blood (for example, how the blood is flowing with respect to the reference direction), or the like.

Further, the display control function 154 may cause an image indicating that the above-described subregion is an undeterminable region, instead of (or in addition to) the above-described images, to be displayed on the display 130 so that the images are superimposed on the image IM10. This makes it possible to cause a more detailed determination result to be displayed.

In the above-described embodiment, the reference direction is set for each subregion included in the region of interest, and an angle formed by the reference direction and the flow direction of the body fluid (for example, the blood flow direction) is compared with a predetermined angle (fixed angle) for a determination of the flow state of the body fluid, but instead, the reference direction may be set as a fixed direction and the predetermined angle may be changed for each subregion for comparison.

In the above-described embodiment, analysis of a nerve bundle in the body may be performed instead of (or in addition to) the analysis of the body fluid. In this case, the body fluid analysis device 100 uses the medical image to set the region of interest including the nerve bundle using the region-of-interest setting function 144 and set a plurality of subregions for the set region of interest using the subregion setting function 146. Further, the body fluid analysis device 100 sets the reference direction for each subregion using the reference direction setting function 148, and determines a flow direction of electrical or neurotransmitter chemical signals in nerves for each subregion using the flow direction determination function 150. Further, the body fluid analysis device 100 determines the flow direction of electrical or chemical signals in the nerve or the nerve bundle in the region of interest on the basis of the reference direction for each subregion set using the reference direction setting function 148 and the flow direction of electrical or chemical signals for each subregion determined using the flow direction determination function 150. This makes it possible to more accurately analyze, for example, an orientation of the nerve bundle in the region of interest.

According to the above-described embodiment, in the body fluid analysis device 100, the region-of-interest setting function 144 of setting a region of interest in a medical image, the subregion setting function 146 of setting one or more subregions in the region of interest set by the region-of-interest setting function 144, the reference direction setting function 148 of setting a reference direction for each of the subregions set by the subregion setting function 146, the flow direction determination function 150 of determining a flow direction of a body fluid for each subregion, and the determination function of determining the state of a flow of the body fluid in the region of interest on the basis of the reference direction for each subregion set by the reference direction setting function 148 and the flow direction of the body fluid for each subregion determined by the flow direction determination function 150 are included such that the state of the flow of the body fluid in the region of interest can be analyzed more accurately.

Further, according to the embodiment, the state of the flow of the body fluid in the region of interest is determined more accurately, making it possible to support medical practice such as a determination of therapeutic effects of a doctor or the like. Further, according to the embodiment, it is possible to determine the flow state of the body fluid more accurately even when the region of interest has a distorted shape.

Any of the embodiments described above can be represented as follows.

A body fluid analysis device including
a storage that stores a program, and
a processor,
wherein the processor is configured to
set one or more subregions in a region of interest in a medical image,
set a reference direction for each of the set subregions,
determine a flow direction of a body fluid for each subregion, and
determine the state of a flow of the body fluid in the region of interest on the basis of the set reference direction for each subregion and the determined flow direction of the body fluid for each subregion, by executing the program.

Although some embodiments of the present invention have been described, these embodiments are presented as examples and are not intended to limit the scope of the invention. These embodiments can be performed in various other forms, and various omissions, replacements, and changes can be made without departing from the gist of the invention. The embodiments or modifications thereof are included in the scope or gist of the invention as well as in the scope of the invention described in the claims and an equivalent scope thereof.

For example, the body fluid analysis device in the present embodiment not only provides a user such as a doctor with the flow state of the body fluid in the region of interest included in the medical image to support diagnosis and the like, but also can be applied in the field of determining therapeutic effects from an analyzed flow state of the body fluid in the field of therapeutic effect simulation through numerical fluid analysis.

What is claimed is:

1. A body fluid analysis device comprising:
processing circuitry configured to:
set one or more subregions in a region of interest in a medical image;
set a reference direction for each of the set subregions;
determine a flow direction of a body fluid for each subregion; and
determine a state of a flow of the body fluid in the region of interest on the basis of the set reference direction for each subregion and the determined flow direction of the body fluid for each subregion.

2. The body fluid analysis device according to claim 1, wherein
the processing circuitry is further configured to:
set the region of interest in the medical image on the basis of one or both of information on a structure of a part within a subject included in the medical image and information on a medical device placed within the subject.

3. The body fluid analysis device according to claim 1, wherein
the region of interest includes a valve orifice region formed by a heart valve.

4. The body fluid analysis device according to claim 1, wherein
the processing circuitry is configured to set the subregion on the basis of one or both of information on a structure of a part within a subject included in the medical image and information on a medical device placed within the subject.

5. The body fluid analysis device according to claim 1, wherein
the processing circuitry is configured to set a distribution of the reference directions in the region of interest on the basis of the reference direction set for each of the subregions.

6. The body fluid analysis device according to claim 1, wherein
the processing circuitry is configured to set a reference direction with respect to a target subregion on the basis of the target subregion and a nearby subregion present within a predetermined range from the target subregion.

7. The body fluid analysis device according to claim 1, wherein
the medical image includes a plurality of medical images having different time phases, and
the processing circuitry is configured to set the reference direction in the subregion on the basis of movement information of the subregion in the plurality of medical images having different time phases.

8. The body fluid analysis device according to claim 1, wherein
the processing circuitry is configured to determine the state of the flow of the body fluid in the subregion on the basis of the reference direction and the flow direction of the body fluid for each subregion and the flow direction of the body fluid in a nearby subregion present around the subregion.

9. The body fluid analysis device according to claim 1, wherein
the processing circuitry is configured to determine a flow state of the body fluid in the subregion on the basis of the reference direction of the subregion, the flow direction of the body fluid in the subregion, and a position of the subregion in the region of interest.

10. The body fluid analysis device according to claim 1, wherein
the processing circuitry is configured to:
acquire one or both of a flow velocity or a flow rate of the body fluid for each subregion; and
determine the state of the flow of the body fluid in the subregion on the basis of the reference direction of the subregion, the flow direction of the body fluid, and one or both of the flow velocity or the flow rate of the body fluid.

11. The body fluid analysis device according to claim 1, wherein
the processing circuitry is further configured to:
generate an image including information on the flow direction of the body fluid in the region of interest determined and cause the generated image to be displayed on a display,
wherein the processing circuitry is configured to generate an image in which a position of the subregion included in the region of interest is associated with information indicating the state of the flow of the body fluid in the subregion.

12. The body fluid analysis device according to claim 11, wherein
the processing circuitry is configured to generate an image indicating the flow direction of the body fluid for each subregion.

13. The body fluid analysis device according to claim 11, wherein
the processing circuitry is configured to change a display aspect of an image indicating the state of the flow of the body fluid on the basis of a determination result.

14. The body fluid analysis device according to claim 13, wherein
the processing circuitry is configured to determine whether the flow of the body fluid is a forward flow or a backward flow for each subregion, and
the processing circuitry is configured to make display aspects of an image indicating the flow of the body fluid different between a case in which a determination result is a forward flow and a case in which the determination result is a backward flow.

15. The body fluid analysis device according to claim 1, wherein
the processing circuitry is configured to determine the state of the body fluid in the region of interest on the basis of the flow state of the body fluid for each subregion.

16. A control method for a body fluid analysis device, the control method comprising:
setting a region of interest in a medical image by a computer of the body fluid analysis device;
setting one or more subregions in a region of interest in a medical image by a computer of the body fluid analysis device;
setting a reference direction for each of the set subregions by the computer;
determining a flow direction of a body fluid for each subregion by the computer; and
determining a state of a flow of the body fluid in the region of interest on the basis of the set reference direction for each subregion and the determined flow direction of the body fluid for each subregion by the computer.

17. A computer-readable non-transient storage medium storing a program, the program causing a computer of a body fluid analysis device to:
set one or more subregions in a region of interest in a medical image;
set a reference direction for each of the set subregions;
determine a flow direction of a body fluid for each subregion; and
determine a state of a flow of the body fluid in the region of interest on the basis of the set reference direction for each subregion and the determined flow direction of the body fluid for each subregion.

* * * * *